(12) United States Patent
Smith et al.

(10) Patent No.: US 10,433,651 B2
(45) Date of Patent: Oct. 8, 2019

(54) SYSTEM AND METHOD FOR SECURING AN UNDERPAD ON A MATTRESS

(71) Applicants: Martasz Smith, Chicago, IL (US); LaShawn Floyd, Chicago, IL (US)

(72) Inventors: Martasz Smith, Chicago, IL (US); LaShawn Floyd, Chicago, IL (US)

( * ) Notice: Subject to any disclaimer, the term of this patent is extended or adjusted under 35 U.S.C. 154(b) by 498 days.

(21) Appl. No.: 15/186,026

(22) Filed: Jun. 17, 2016

(65) Prior Publication Data

US 2017/0360211 A1    Dec. 21, 2017

(51) Int. Cl.
| | | |
|---|---|---|
| *A47C 21/02* | (2006.01) | |
| *A47C 31/10* | (2006.01) | |
| *F16B 1/00* | (2006.01) | |
| *A61F 5/48* | (2006.01) | |
| *F16B 2/08* | (2006.01) | |
| *F16B 11/00* | (2006.01) | |
| *F16B 21/07* | (2006.01) | |

(52) U.S. Cl.
CPC .......... *A47C 21/022* (2013.01); *A47C 21/028* (2013.01); *A47C 31/105* (2013.01); *A61F 5/48* (2013.01); *A61F 5/485* (2013.01); *F16B 1/00* (2013.01); *F16B 2/08* (2013.01); *F16B 11/006* (2013.01); *F16B 21/07* (2013.01); *F16B 2001/0028* (2013.01); *F16B 2001/0035* (2013.01)

(58) Field of Classification Search
CPC ....... A47C 31/105; A47C 21/00; A47C 21/02; A47C 21/022; A47C 21/028; A47C 21/06; F16B 1/00; F16B 2/08; F16B 2001/0035; F16B 21/07; F16B 11/006; F16B 2001/0028; A47G 9/0246; A47G 9/04; A47G 2009/0269; A61F 5/48; A61F 5/485

See application file for complete search history.

(56) References Cited

U.S. PATENT DOCUMENTS

| | | | | |
|---|---|---|---|---|
| 1,562,809 | A * | 11/1925 | Thompson | A61G 7/05723 5/484 |
| 1,621,149 | A * | 3/1927 | Blissitt | A47C 21/06 428/478.4 |
| 1,742,064 | A * | 12/1929 | Dinstuhl | A47G 9/0238 5/498 |
| 1,841,410 | A * | 1/1932 | Karr | A47C 21/022 297/224 |
| 2,024,050 | A * | 12/1935 | May | A47C 21/022 24/72.5 |
| 2,188,576 | A * | 1/1940 | Mulloy | A47C 21/022 24/72.5 |
| 2,284,778 | A * | 6/1942 | Treiber | A47C 21/022 297/224 |

(Continued)

*Primary Examiner* — Nicholas F Polito
*Assistant Examiner* — David R Hare
(74) *Attorney, Agent, or Firm* — Foley & Lardner LLP

(57) ABSTRACT

An apparatus comprises a mattress. An underpad is positioned on the mattress such that a lower surface of the underpad is in contact with the mattress. A securing assembly is interposed between the mattress and the underpad. The securing assembly comprises a plurality of securing member positioned on the lower surface of the underpad, and a plurality of mating securing members positioned on the mattress. Each of the plurality of securing members engages a corresponding mating securing member so as to be removably coupled thereto, thereby immovably positioning the underpad on the mattress.

13 Claims, 9 Drawing Sheets

(56) References Cited

U.S. PATENT DOCUMENTS

| | | | | |
|---|---|---|---|---|
| 2,414,927 A * | 1/1947 | Chapman | A47C 27/005 | 5/484 |
| 2,537,652 A * | 1/1951 | Churchill | A47C 27/005 | 5/499 |
| 2,789,292 A * | 4/1957 | Budinquest | A47D 15/02 | 5/486 |
| 3,143,747 A * | 8/1964 | McSorley | A47D 15/02 | 5/498 |
| 3,491,412 A * | 1/1970 | Johnson | A47C 21/00 | 24/324 |
| 4,199,830 A * | 4/1980 | Ogata | A47C 21/022 | 24/72.5 |
| 4,391,010 A * | 7/1983 | Kronman | A47G 9/0238 | 5/484 |
| 4,524,474 A * | 6/1985 | Svensson | A61F 5/485 | 5/484 |
| 4,599,756 A * | 7/1986 | Koffler | A47C 27/007 | 5/484 |
| 4,712,261 A * | 12/1987 | Castro | A47C 17/22 | 24/72.5 |
| 4,884,305 A * | 12/1989 | Blackmon | A47C 21/022 | 5/496 |
| 5,092,010 A * | 3/1992 | Wong | A47G 9/0284 | 5/493 |
| 5,099,532 A * | 3/1992 | Thomas | A61F 5/485 | 5/484 |
| 5,221,273 A * | 6/1993 | Graham | A47C 27/005 | 5/484 |
| 5,321,862 A * | 6/1994 | Campbell | A47C 21/022 | 5/482 |
| 5,327,595 A * | 7/1994 | Allen | A47C 21/022 | 24/72.5 |
| 5,476,456 A * | 12/1995 | Rankin | A47C 27/005 | 128/849 |
| 5,497,521 A * | 3/1996 | Waits | A47C 21/048 | 2/69.5 |
| 5,732,424 A * | 3/1998 | Bond | A47G 9/02 | 5/498 |
| 6,014,782 A * | 1/2000 | Stevenson | A47C 27/008 | 5/482 |
| 6,233,762 B1 * | 5/2001 | Bradley | A47C 21/022 | 5/484 |
| 6,575,533 B1 * | 6/2003 | Kicos | A47C 7/383 | 297/188.06 |
| 6,739,002 B1 * | 5/2004 | Pannu | A47C 21/022 | 5/494 |
| 6,845,532 B1 * | 1/2005 | Rosenblum | A47C 27/008 | 40/661 |
| 6,922,862 B1 * | 8/2005 | Thompson | A47C 27/005 | 5/500 |
| 8,627,521 B2 * | 1/2014 | Rowson | A47G 9/02 | 5/488 |
| 8,635,724 B2 * | 1/2014 | Moorhouse | A47G 9/02 | 5/482 |
| 8,856,984 B1 * | 10/2014 | Donham | A47G 9/0246 | 5/496 |
| 9,545,164 B2 * | 1/2017 | Tulloch | A47G 9/0246 | |
| 2008/0222805 A1 * | 9/2008 | Saunders | A47C 27/007 | 5/484 |
| 2010/0154125 A1 * | 6/2010 | Fratovich | A47C 21/022 | 5/691 |
| 2015/0374568 A1 * | 12/2015 | Miralles | A61G 7/02 | 4/452 |
| 2016/0286988 A1 * | 10/2016 | Robert | A47G 9/02 | |
| 2017/0368783 A1 * | 12/2017 | Pool | B32B 3/06 | |

* cited by examiner

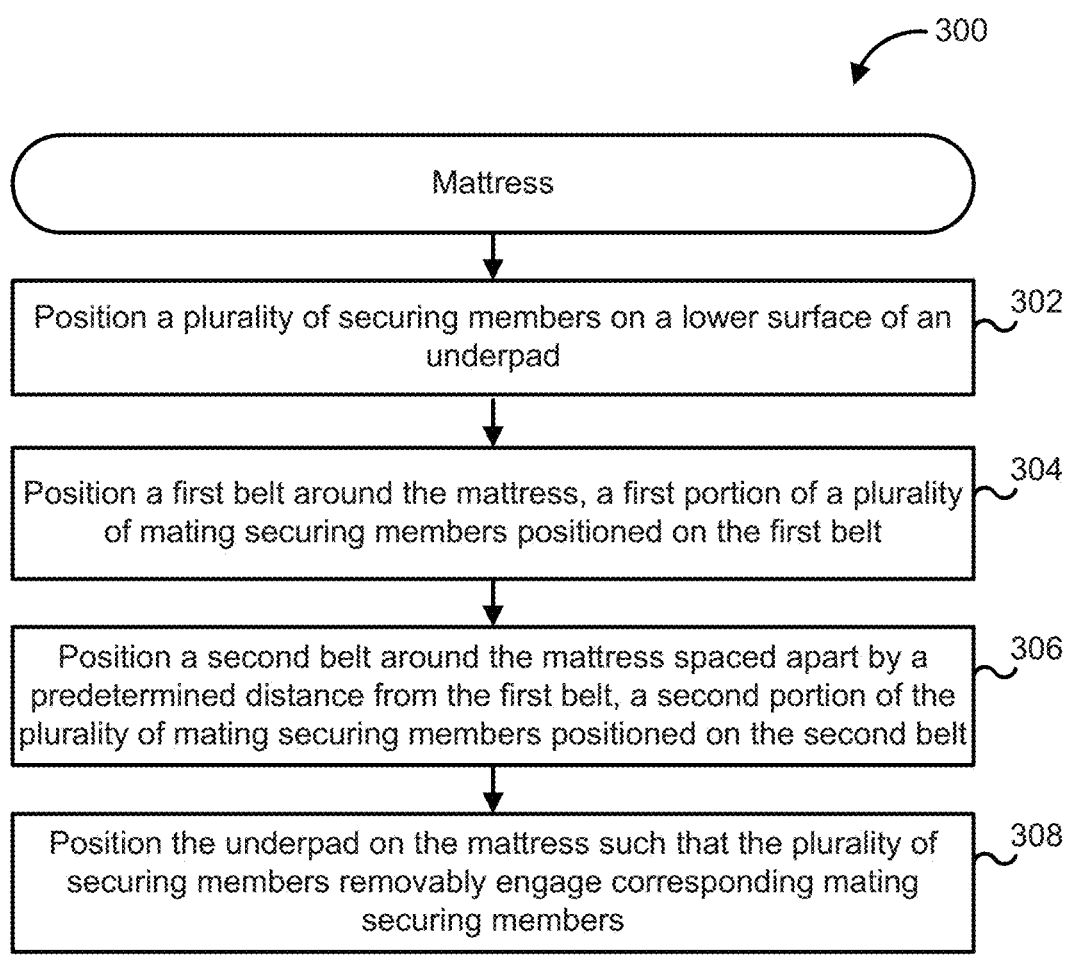

SYSTEM AND METHOD FOR SECURING AN UNDERPAD ON A MATTRESS

TECHNICAL FIELD

The present disclosure relates generally to systems and methods for securing underpads on mattresses.

BACKGROUND

Seniors, terminally ill patients, paraplegic patients, patients in hospice care or patients suffering from incontinence or involuntary bowel movements often soil the bedding of their mattresses. An underpad may be positioned on the mattress, for example on a bed sheet (e.g., a fitted sheet) positioned over the mattress so as to absorb urine or bowel movement and prevent leakage to the bed sheet and the mattress positioned therebeneath. A dirty underpad is then replaced with a new underpad. Underpads are generally prone to slipping, sliding, bunching or shifting over the mattress exposing the bed sheet and the mattress on which they are positioned. Furthermore, movement of the underpad may be discomforting to the patient and/or a care giver thereof, who may have to reposition the patient and/or the underpad so that the patient and the underpad are positioned on the center of mattress, and minimize movement to ensure coverage and protection.

SUMMARY

Embodiments described herein relate generally to systems and methods for immovably securing an underpad on a mattress and, in particular to a securing assembly including securing members positioned on the underpad. Corresponding mating securing members are positioned on a positioning assembly secured to the mattress. The securing members and mating securing members removably engage each other so as to immovably secure the underpad on the mattress.

In some embodiments, a system comprises a mattress. An underpad is positioned on the mattress such that a lower surface of the underpad is in contact with the mattress. A securing assembly is interposed between the mattress and the underpad. The securing assembly comprises a plurality of securing members positioned on the lower surface of the underpad, and a plurality of mating securing members positioned on the mattress. Each of the plurality of securing members engage a corresponding mating securing member so as to be removably coupled thereto, thereby immovably positioning the underpad on the mattress.

In some embodiments, a securing assembly for securing an underpad to a mattress comprises a plurality of securing member structured to be positioned on a lower surface of the underpad. A positioning assembly is structured to be positioned around the mattress. A plurality of mating securing members are positioned on the positioning assembly. Each of the plurality of securing members is structured to engage a corresponding mating securing member so as to be removably coupled thereto, thereby immovably positioning the underpad on the mattress.

In some embodiments, a method for securing an underpad on a mattress comprises positioning a plurality of securing members on a lower surface of the underpad. A first belt is positioned around the mattress. A first portion of a plurality of mating securing members is positioned on the first belt. A second belt is positioned around the mattress spaced apart from the first belt by a predetermined distance. A second portion of the plurality of mating securing members is positioned on the second belt. The underpad is positioned on the mattress such that the plurality of securing members engage corresponding mating securing members so as to be removably coupled thereto, thereby immovably positioning the underpad on the mattress.

In some embodiments, an underpad for preventing soiling of a mattress comprises a water proof layer comprising a first surface and a second surface opposite the first surface. The second surface is structured to be positioned on at least one of the mattress or a bed sheet disposed on the mattress, such that the first surface faces away from the mattress. An absorbent material is positioned on the first surface of the water proof layer. A plurality of securing members are positioned on the second surface of the water proof layer. Each of the plurality of securing members are structured to engage a corresponding mating securing member positioned on the mattress or interposed between the mattress and the underpad.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 9 is a schematic flow diagram of a method of securing an underpad on a mattress, according to an embodiment.

Figure 1:
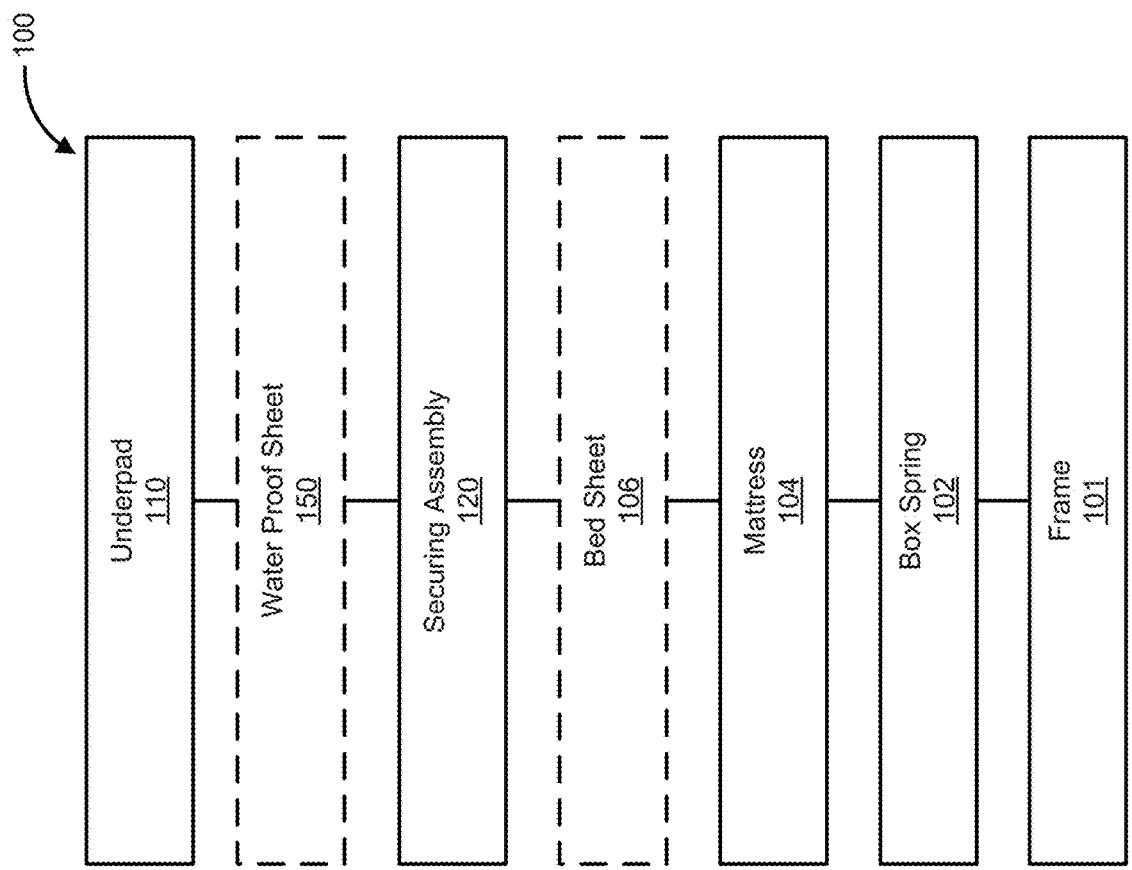
FIG. 1 is a schematic block diagram of a system including a mattress and an underpad positioned on the mattress secured thereto via a securing assembly, according to an embodiment.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to systems and methods for immovably securing an underpad on a mattress and, in particular to a securing assembly including securing members positioned on the underpad. Corresponding mating securing members are positioned on a positioning assembly secured to the mattress. The securing members and mating securing members removably engage each other so as to immovably secure the underpad on the mattress.

Various embodiments of the systems and methods of securing an underpad on a mattress may provide benefits including, for example: (1) allowing removable securing of an underpad on the mattress via securing members, thereby providing easy securing and removal of the underpad from the mattress; (2) allowing adjusting of a length of belts included in the positioning assembly so as to be compatible with mattresses having various sizes, for example single, twin, full, queen, king, etc.; (3) allowing positioning of mating securing members at pre-determined spacing relative to corresponding securing members of the underpad via a positioning assembly; and (4) significantly increasing comfort of patients and reducing accidents by preventing slipping of the underpad relative to the mattress.

FIG. 1 is a schematic block diagram of an apparatus system 100 that includes a mattress 104, an underpad 110, a securing assembly 120, and optionally a water proof sheet 150. The mattress 102 may be positioned on a box spring 102, or on slats positioned on a frame 101. In some embodiments, the box spring 102 may be positioned on the frame 101. The box spring 102 may comprise any suitable box spring, for example a wooden box spring or any other commonly available box spring. The frame 101 may include any suitable frame, for example a metallic or wooden frame which may include legs positioned on a surface, for example a floor of a room.

The mattress 104 may include any suitable mattress such as for example a spring mattress, a foam mattress, a memory foam mattress, a gel mattress, a water mattress, an air mattress or any other suitable mattress. The mattress 104 may have any suitable size, for example single, twin, full, queen, king or any other suitable shape or size. A bed sheet 106, for example a fitted bed sheet may be positioned on the mattress.

An underpad 110 is positioned on the mattress 104, for example on the bed sheet 106 disposed on the mattress 104. The underpad 110 may include any suitable underpad as is commonly known in the arts. For example, the underpad 110 may include a water proof layer, for example a plastic sheet. An absorbent material (e.g., gels, foams, cotton, etc.) may be positioned on an upper surface of the underpad 110. The underpad 110 is positioned on the mattress 104 such that a lower surface of the underpad 110 is in contact with the mattress 104 or otherwise the bed sheet 106 disposed on the mattress 104. The absorbent material may be encased in a mesh positioned on the water proof layer, or adhered to an upper surface of the water proof layer.

A securing assembly 120 is interposed between the mattress 104 and the underpad 110. The securing assembly 120 includes a plurality of securing members positioned on the lower surface of the underpad 110, and a plurality of mating securing members positioned on the mattress 104. The securing members and the mating securing members may include, for example pieces of VELCRO®, magnets, snap buttons, hooks, clips or any other suitable securing assembly.

Each of the plurality of securing members is structured to engage a corresponding mating securing member so as to be removably coupled thereto, thereby immovably positioning the underpad 110 on the mattress 104. For example, one embodiment may utilize hook-and-loop fasteners, where the securing members include VELCRO® loops and the mating securing members may include VELCRO® hooks, or vice versa. The securing members 222 may be coupled to the lower surface of the underpad 110 via adhesive such as glue, mechanical connection such staples, pins, sowing thread, or any other suitable coupling mechanism such as magnets and a ferromagnetic surface.

The securing members may be positioned at any suitable location on the lower surface of the underpad 110, for example at corners thereof. The mating securing members may be disposed on the mattress 104, or on the bed sheet 106 disposed on the mattress. The mating securing members may be positioned on the mattress 104 or the bed sheet 106 so as to correspond to the positioning of the plurality of securing members on the lower surface of the mattress 104.

In some embodiments, the securing assembly 120 further comprises a positioning assembly positioned over the mattress 104 such that the plurality of mating securing members are positioned on the positioning assembly. In particular embodiments, the positioning assembly may include a belt positioned around the mattress 104 and coupled to itself. At least a portion of the plurality of mating securing members may be positioned on the belt located at positions corresponding to the locations of at least a portion of the plurality of securing members positioned on the lower surface of the underpad 110.

The belt may be formed from any suitable material or combination of materials, for example leather, polymer, nylon, cotton, silk, elastic, plastic, hook-and-loop fasteners, etc. The belt maybe formed from an inflexible material or flexible material. In some embodiments, the belt may positioned orthogonal to a longitudinal axis of the mattress 104, and wrapped around the mattress 104. In other embodiments, the belt may be positioned parallel to the longitudinal axis of the mattress 104.

The positioning assembly may further includes a snap positioned on a first end of the belt, and a stud positioned on a second end of the belt opposite the first end. The snap is structured to removably engage the stud so as to removably secure the belt around the mattress 104. In other embodiments, the positioning member may include any other coupling mechanism, for example buttons, zips, clips, hooks, VELCRO® or any other mechanism for coupling the first end of the belt to the second end.

A length adjusting mechanism may be operatively coupled to the belt. The length adjusting mechanism may be configured to adjust a length of the belt positioned around the mattress 104 so as to correspond to a width of the mattress 104. The length adjusting mechanism may, therefore allow adjusting of the length of the belt to correspond to a width of the mattress 104. In this manner, the same positioning member may be compatible with a mattress 104 having any width. In some embodiments, the length adjusting mechanism may include a ring, a slider, a strap adjuster, and/or a winch.

In some embodiments, the positioning assembly includes a first belt and a second belt. The first belt may be positioned around the mattress 104 at a first location thereof. A first portion of the plurality of mating securing members, which correspond to a first portion of the plurality of securing members may be positioned on the first belt. The positioning assembly may further include a second belt positioned around the mattress 104 and spaced apart from the first belt. A second portion of the plurality of mating securing members corresponding to a second portion of the plurality of securing members may be positioned on the second belt.

In this manner, the first belt and the second belt may be spaced apart, for example by a predetermined distance corresponding to a distance between the first portion of the securing members (e.g., positioned on a first end of the underpad proximate to a first end of the mattress 104) and the second portion of the securing members (e.g., positioned on a second end of the underpad 110 opposite the first end).

In particular embodiments, a ribbon may be coupled to each of the first belt and the second belt and positioned orthogonal to each of the first belt and the second belt. The ribbon may have a ribbon length configured to space the first belt and the second belt apart by a predetermined distance corresponding to a spacing between the first portion of the plurality of securing members, and the second portion of the plurality of securing members. The ribbon may serve as a spacer configured to space the first belt and the second belt by the predetermined distance.

In some embodiments, a water proof sheet 150 may be interposed between the securing assembly 120 (e.g., the positioning assembly disposed over the mattress 104) and the underpad 210 so as to provide an additional waterproof layer for protecting the mattress 104, for example in situations when there is overflow of waste fluids from the underpad 110. The water proof sheet 150 may include a single layer or multilayer plastic sheet, water proof cloth, an absorbent sheet, or formed from any other suitable water proof material.

The water proof sheet 150 may include a plurality of first securing members (not shown) positioned on a first surface of the water proof sheet 150 facing the securing assembly 120. In some embodiments, the first securing members may correspond to the plurality of mating securing members positioned on the positioning assembly (e.g., comprise hook and loop securing members, snaps, buttons, magnets, etc.). The first securing members may be removably coupled to the plurality of mating securing members, or any other corresponding mating securing members positioned on the mattress 104 as to immovably position the water proof sheet 150 on the securing assembly 120 (e.g., the positioning assembly) and, thereby on the mattress 104.

The water proof sheet 150 may also comprise a plurality of second securing members (not shown) positioned on a second surface of the water proof sheet 150 opposite the first surface. The second securing members may be positioned on the second surface at locations corresponding to the locations of the securing members of the underpad 110. The second securing members (e.g., hook and loop securing members such as VELCRO®) may be configured to be removably coupled to the securing members of the underpads 110 so as to immovably position the underpad 110 on the water proof sheet 150 and, thereby the mattress 104 via the securing assembly 120. In this manner, the water proof sheet 150 may provide added protection to the mattress 104 from soiling even in situations when the waste fluids overflow the underpad 110.

Figure 2:
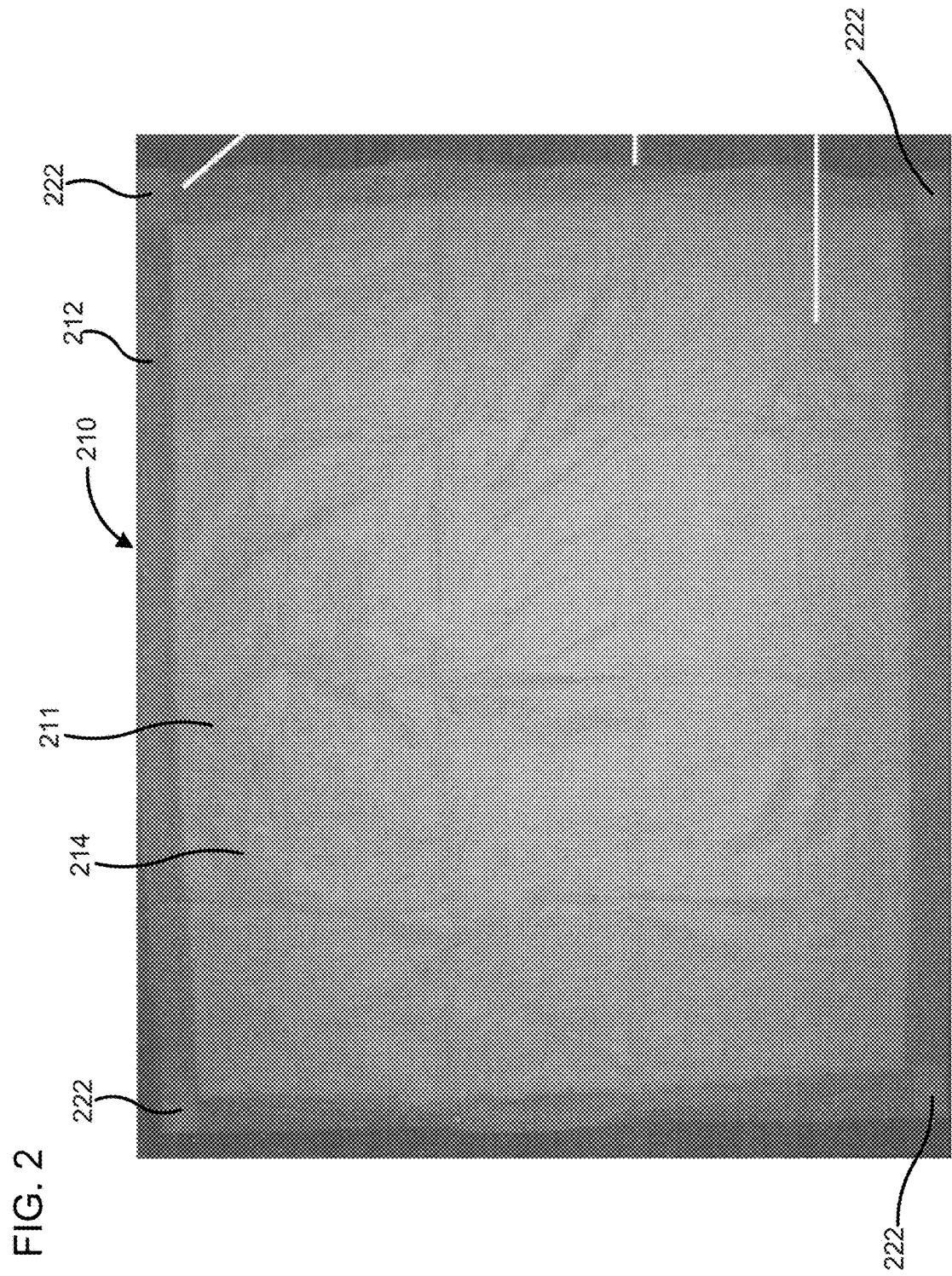
FIG. 2 is an image of a lower surface of an underpad with a plurality of securing members positioned thereon, according to an embodiment.
Figure 3:
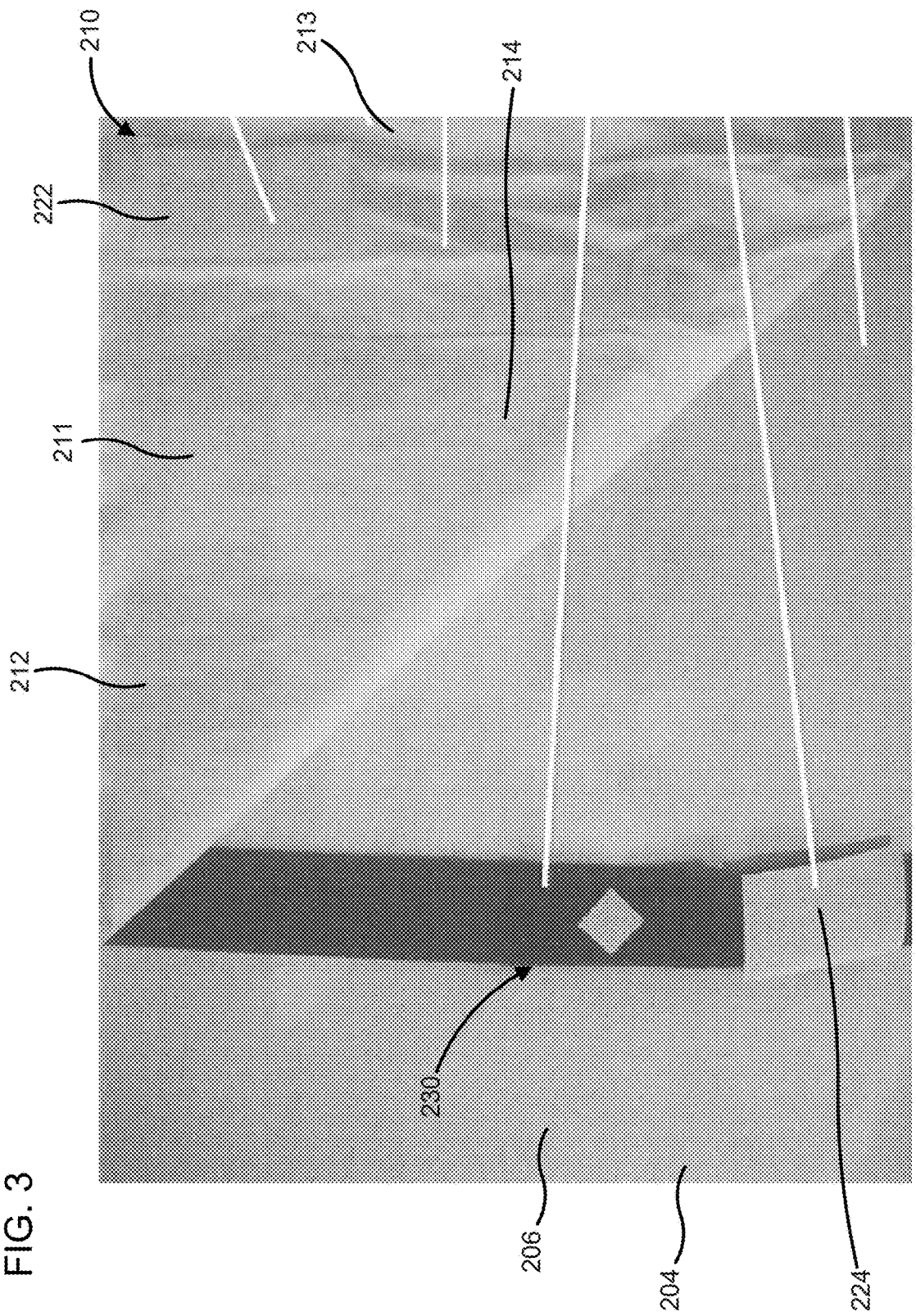
FIG. 3 is an image of a portion of a mattress having a fitted sheet disposed thereon, and a positioning assembly positioned around the mattress. A portion of a lower surface of the under pad of FIG. 2 is also shown to show the securing member corresponding to the mating securing member positioned on the belt.

FIG. 2 is an image of a lower surface 211 of an underpad 210, according to an embodiment. FIG. 3 is an image of a portion of a mattress 204 having a bed sheet 206 (e.g., a fitted bed sheet) disposed thereon, and the underpad 210 positioned on the bed sheet 206. A positioning assembly 230 is positioned around the mattress 204. The underpad 210 is positioned on the bed sheet 206 disposed on the mattress 204. The mattress 204 may be substantially similar to the mattress 104 described with respect to FIG. 1. The mattress 204 may have any suitable size, for example single, twin, full, queen, king or any other suitable shape or size. The mattress 204 may be positioned on a box spring 202 (FIG. 4) or on slats positioned on a frame (e.g., the frame 101). In some embodiments, the box spring 202 may be positioned on the frame.

The underpad 210 includes a waterproof layer 212 (e.g., a plastic layer) with an absorbent pad 214 (e.g., a gel pad, a foam pad, a cotton pad, etc.) disposed thereon. An absorbent pad 214 may be positioned on an upper surface 213 of the underpad 210. The absorbent pad 214 may be encased on the water proof layer, for example within a mesh or gauze positioned around the absorbent pad 214 and fixedly coupled to the waterproof layer 212. The underpad 210 is positioned on the mattress 204 such that a lower surface 211 of the underpad 210 is positioned on the bed sheet 206 disposed on the mattress 204.

A plurality of securing members 222 are positioned on the lower surface 211 of the underpad 210 (FIG. 2). The securing members 222 may include VELCRO®, as shown in FIGS. 2 and 3. In other embodiments, the securing members 222 may include magnets, snap buttons, hooks, clips or any other suitable securing member. Each of the plurality of securing members 222 is structured to engage a corresponding mating securing member 224 positioned on a positioning member 230 disposed around the mattress 204, as shown in FIGS. 3-7.

The mating securing members 224 may include VELCRO®, as shown in FIG. 3 but may include any other suitable mating securing member (e.g., magnets, snap buttons, hooks, clips or any other suitable mating securing member). The securing members 222 engage a corresponding mating securing member 224 so as to be removably secured thereto, thereby immovably positioning the underpad 210 on the mattress 204.

Figure 4:
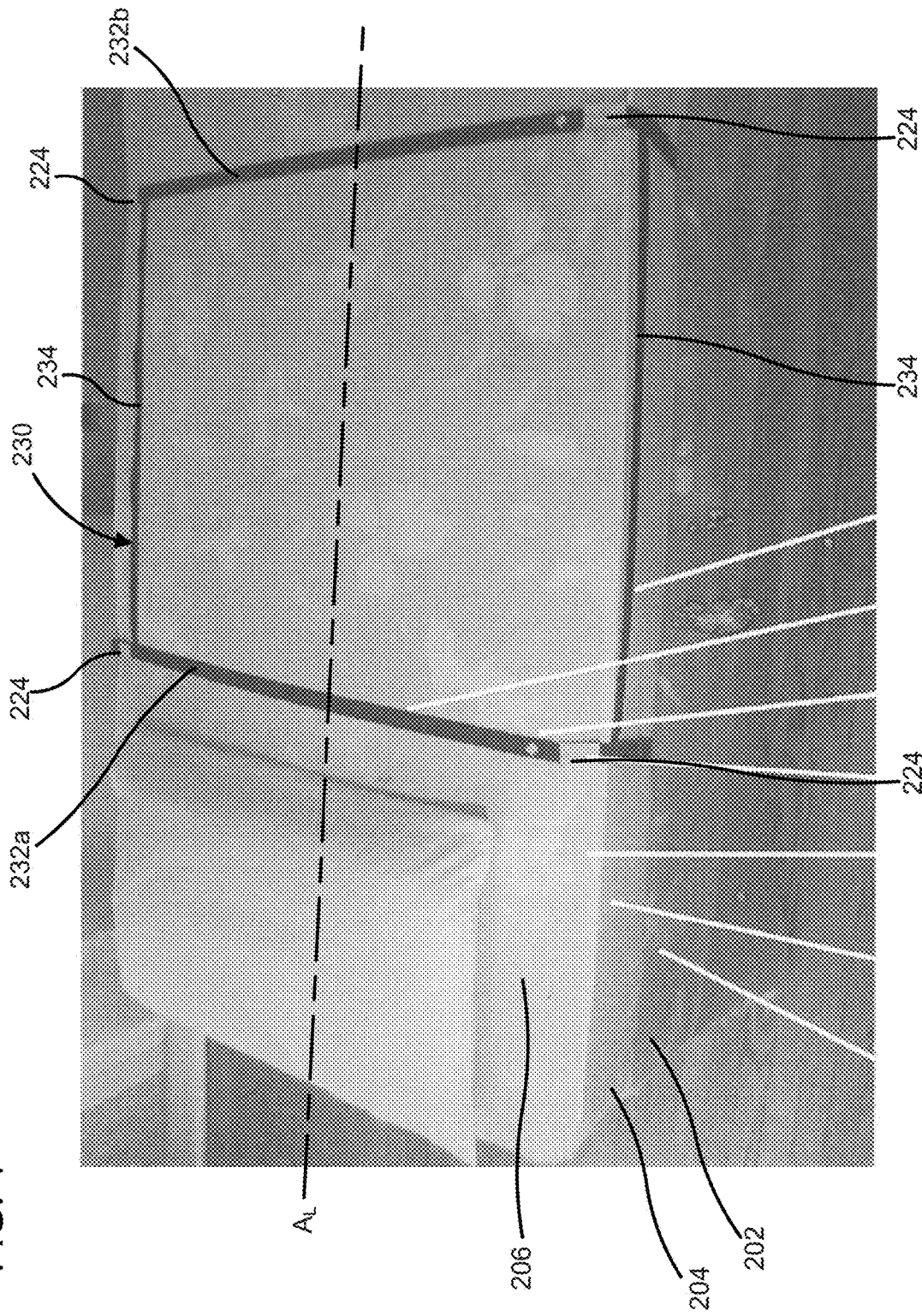
FIG. 4 is a perspective image of the mattress of FIG. 3 with the bed sheet positioned thereon. The positioning assembly including a first belt and a second belt is positioned around the mattress and secured thereto.
Figure 5:
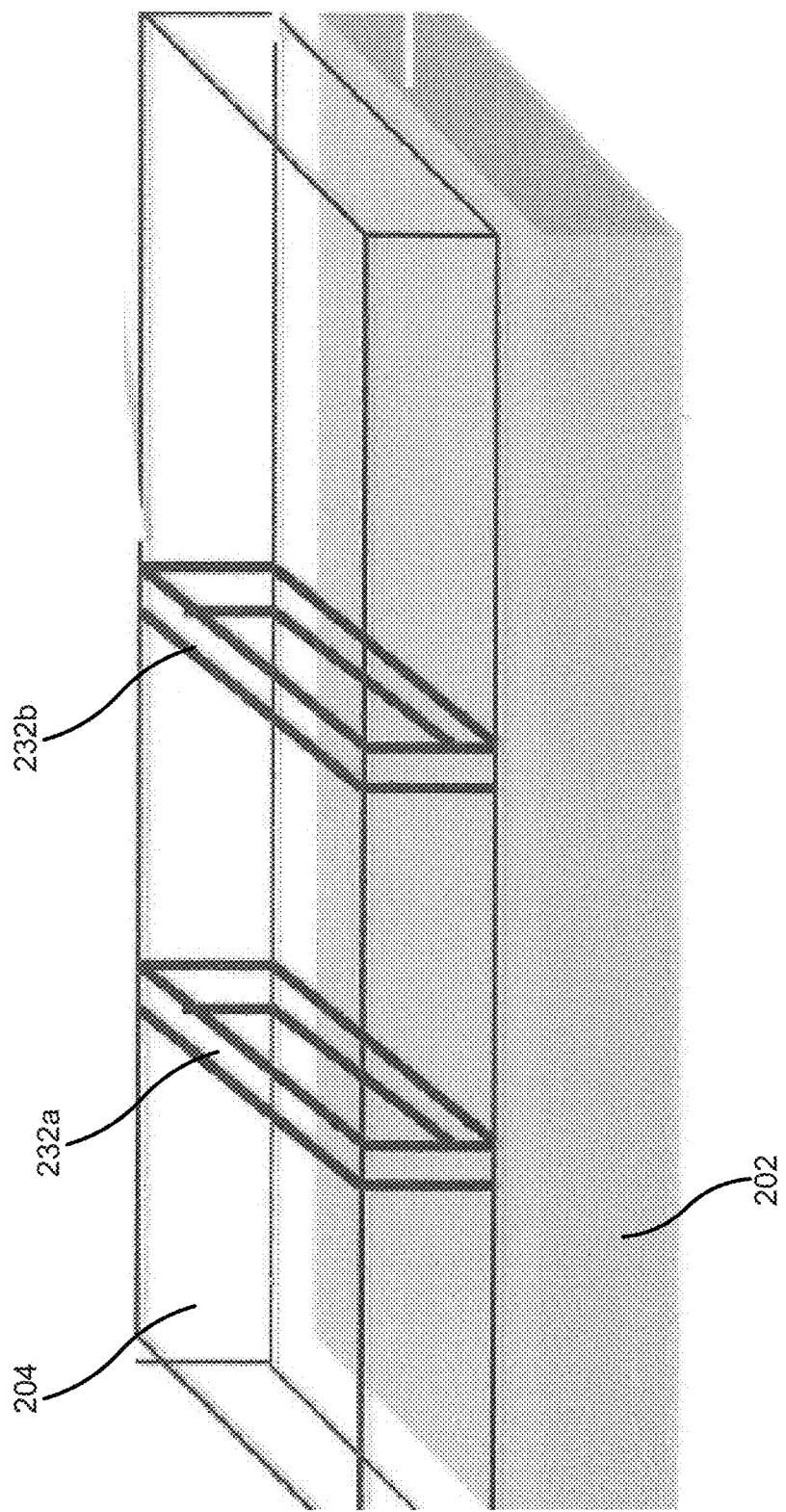
FIG. 5 is a 3-D wire diagram showing the positioning of the first belt and the second belt of the positioning assembly around the mattress.

The positioning assembly 230 is positioned around the mattress 204 such that the plurality of mating securing members 224 are positioned on the positioning assembly 230. FIG. 4 is a perspective image of the mattress 204, and the positioning assembly 230. The positioning assembly 230 includes a first belt 232a positioned around the mattress 204 and removably coupled to itself so as to be secured to the mattress 204. The positioning assembly 230 further includes a second belt 232b positioned around the mattress 204 spaced apart from the first belt 232a. FIG. 5 is a 3-D wire diagram showing the positioning of the first belt 232a and the second belt 232b (collectively referred to herein as "the belts 232") of the positioning assembly 230 around the mattress 204.

The belts 232 may be formed from any suitable material, for example leather, polymer, nylon, cotton, silk, elastics, plastics, VELCRO®, etc. The belts 232 maybe formed from an inflexible material or flexible material. As shown in FIG. 4, the belts 232 are positioned orthogonal to a longitudinal axis of the mattress 204, and wrapped therearound. In other embodiments, the belts 232 may be positioned parallel to the longitudinal axis of the mattress 204. In one embodiment, the securing members 222 are integral with the underpaid 210.

The securing embers 222, the matting securing members 224, and the belts 232 may one or all be constructed from a resistant material, such as a water resistant material or be coated with a resistant coating.

As shown in FIG. 4, a first portion of the plurality of mating securing members 224 may be positioned on the first belt 232a located at positions corresponding to a first portion of the plurality of securing members 222 disposed at a first location on the lower surface 211 of the underpad 210. Similarly, a second portion of the plurality of securing members 222 are positioned on the second belt 232b corresponding to a second portion of the plurality of securing members 222 disposed on a second location of the lower surface 211 of the underpad 210.

The first belt 232a and the second belt 232b are spaced apart from each other by a predetermined distance corresponding to a distance between the first portion of the securing members 222 (e.g., positioned on a first end of the underpad 210 proximate to a first end of the mattress 204) and the second portion of the securing members 222 (e.g., positioned on a second end of the underpad 210 opposite the first end). At least one ribbon 232 is coupled to each of the first belt 232a and the second belt 232b and positioned orthogonal to each of the belts 232. The ribbon 234 may have a ribbon length configured to space the first belt 232a and the second belt 232b apart by a predetermined distance corresponding to a spacing between the first portion of the plurality of securing members 222, and the second portion of the plurality of securing members 222. In other words, the at least one ribbon 234 may serve as a spacer to space the belts 232 apart by the predetermined distance. The ribbon 234 may be formed from any suitable material such as plastic, cloth, polyester, silk, elastic, etc.

Figure 6:
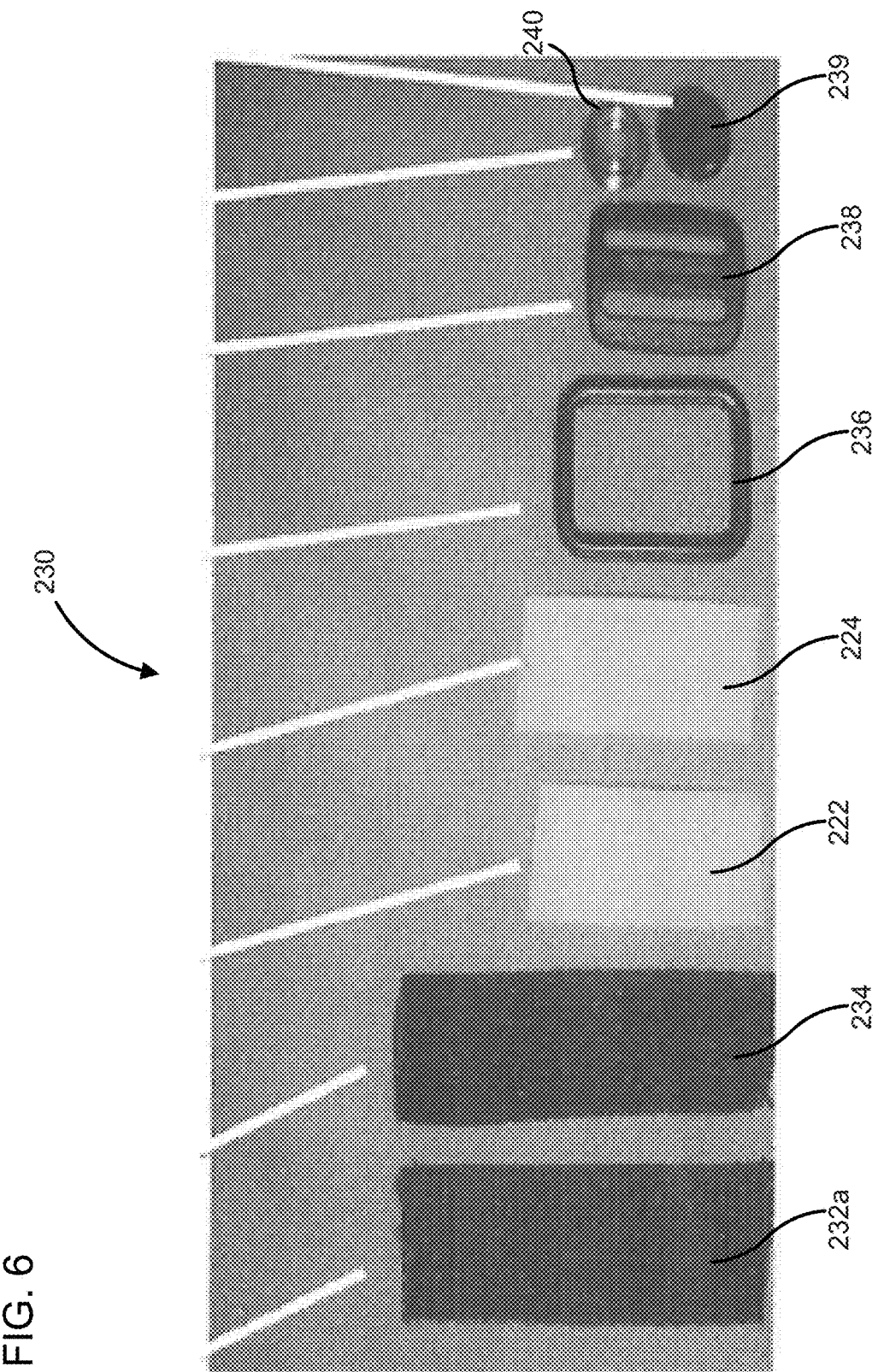
FIG. 6 is an image of various parts which may be included in a positioning system, as well as a securing member and a mating securing member.

FIG. 6 is an image of various parts which may be included in the positioning system 230, as well as a securing member 222 and a mating securing member 224. As shown in FIG. 6, the positioning assembly 230 may further include a ring 236 and a slide 238 configured to slide over the belts 232 so as to adjust a length of the belts 232. In this manner, the length of the belts 232 may be adjusted to correspond to a mattress having any width. For example, each of the belts 232 may be looped around the ring 236 which may be paired with the slide 238 and configured to allow adjusting of a length of the belts 232 around the mattress 204.

A snap 239 may be positioned on a first end of the each of the belts 232, and a stud 240 may be positioned on a second end of the each of the belts 232 opposite the first end. The snap 239 is structured to removably engage the stud 240 so as to removably secure the belts 232 around the mattress 204. In other embodiments, the positioning member may 240 include any other coupling mechanism, for example buttons, zips, clips, hooks, VELCRO® or any other mechanism for coupling the first end of the belts 232 to the second end.

Figure 7:
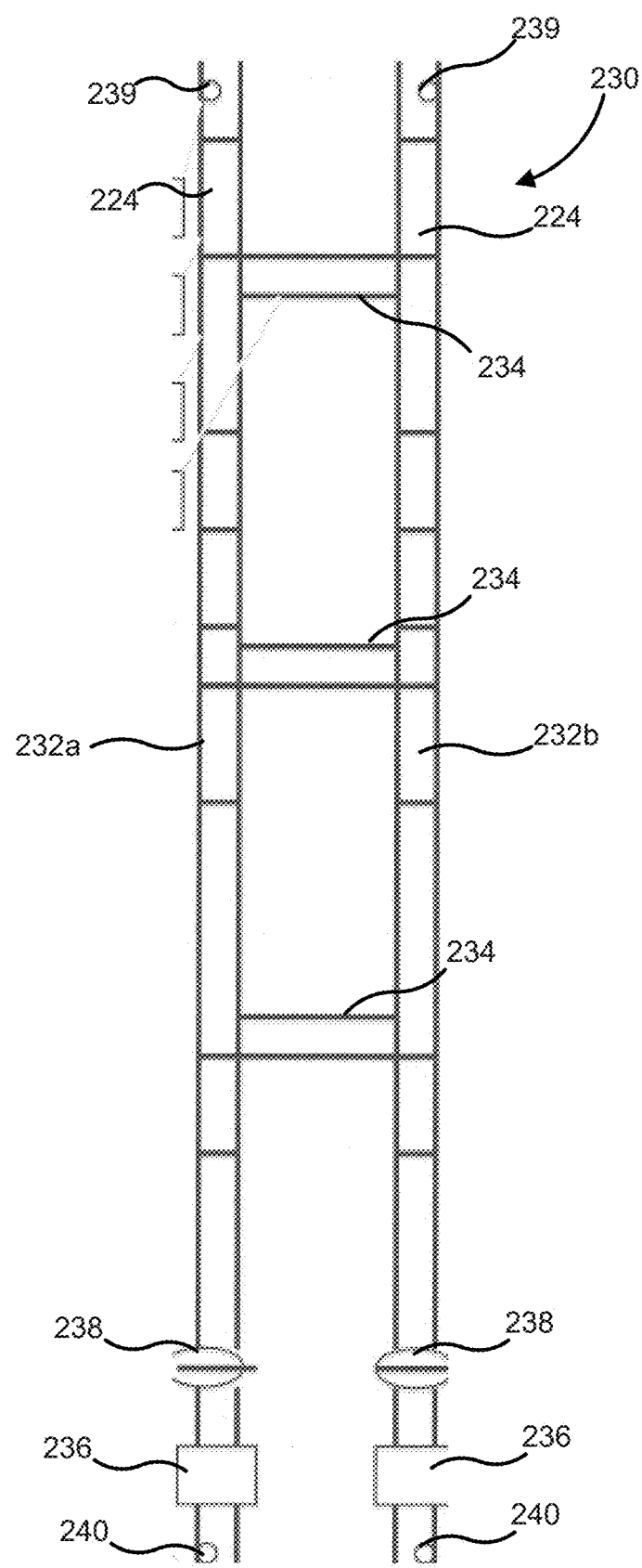
FIG. 7 is a schematic illustration showing positioning of various components of the positioning assembly on the first belt and the second belt thereof.

FIG. 7 is a schematic illustration showing possible positions of various components of the positioning assembly 230 on the first belt 232a and the second belt 232b. The belts 232 are separated by the three ribbons 234 positioned orthogonal thereto, but any number of ribbons 234 may be positioned between the first belt 232a and the second belt 232b. The snaps 239 and the studs 240 are positioned on opposite ends of the belts 232. The rings 239 and sliders 240 are positioned on the first end of the belts 232. The rings 239 and sliders 240 are structured to engage the second end of the respective belts 232 and configured to enable adjustment of a length thereof. The mating securing members 224 are positioned proximate to the second end of the belts 232 corresponding to a position of the securing members 222 positioned on the lower surface 211 of the underpad 230. In some embodiments, 10 or even more mating securing members may be disposed on the positioning assembly 230.

In various embodiments, a plurality of underpads 210 may be disposed on the mattress 204, particularly for large size mattresses. In such embodiments, each of the underpads 210 may include the securing members 222 positioned on a lower surface thereof. Furthermore, the mating securing members 224 disposed on the belts 232 of the positioning assembly 230 may correspond to the securing members 222 of each of the plurality of underpads 210.

Figure 8A:
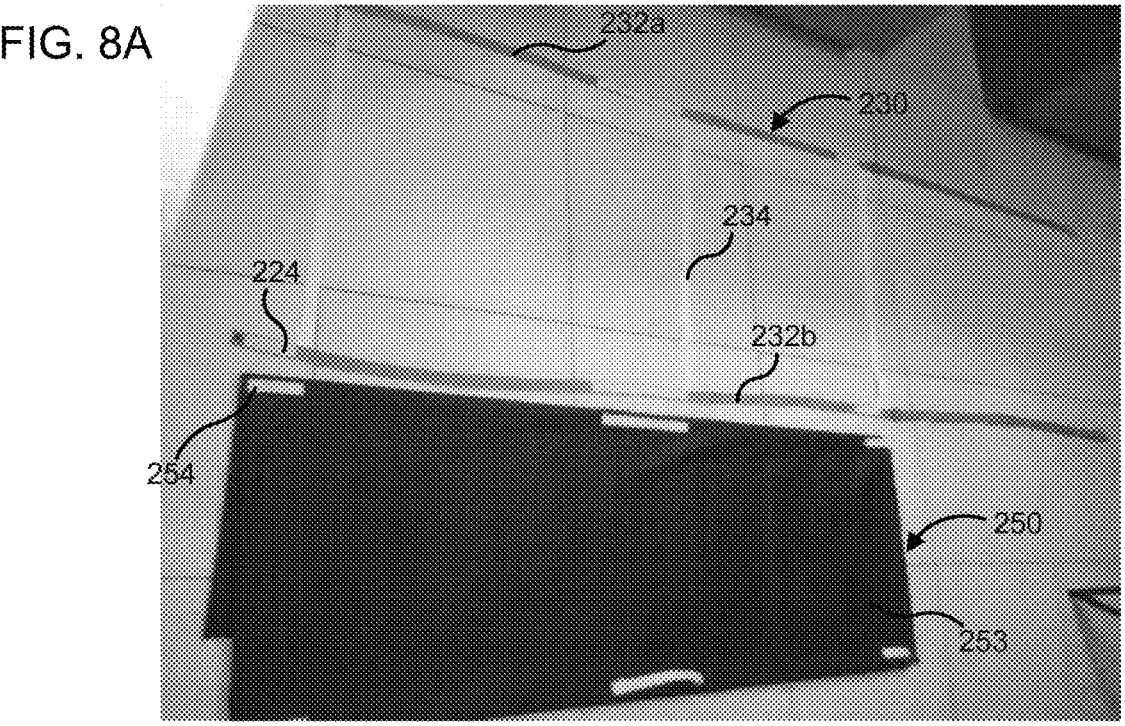
FIG. 8A is an image of the positioning assembly of FIG. 4 and a water proof sheet configured to be positioned between the positioning assembly and the underpad of FIG.
Figure 8B:
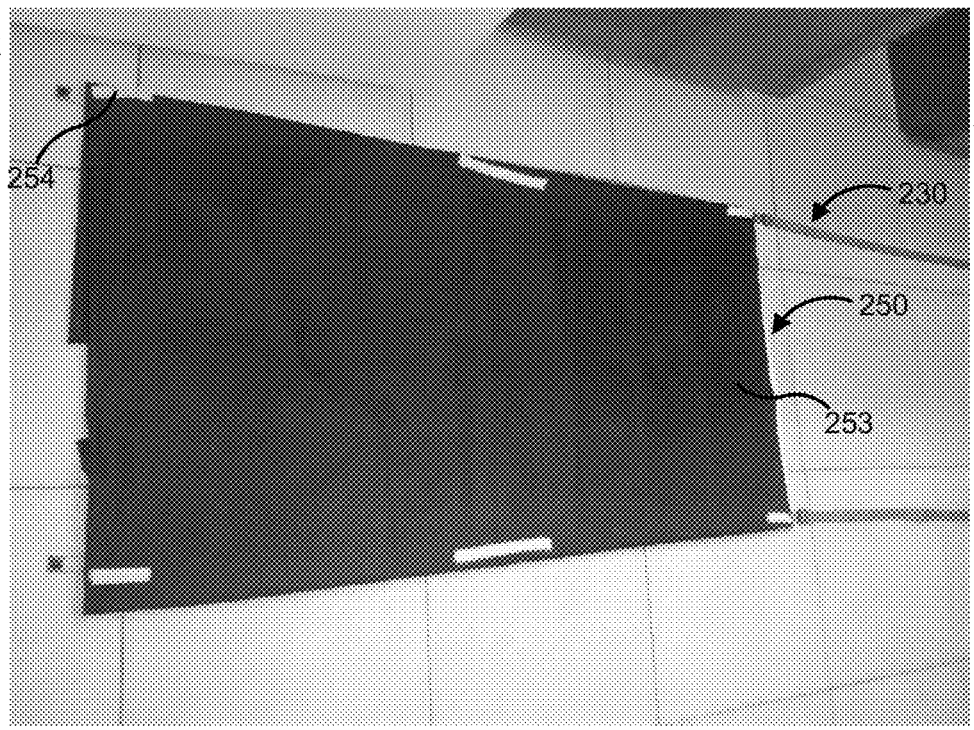
FIG. 8B is another image of the positioning assembly of FIG. 8A with the water proof sheet positioned thereon and coupled thereto.

In some embodiments, a water proof sheet may be interposed between the positioning assembly 230 and the underpad 210 so as to provide an additional waterproof layer for protecting the mattress 204, for example in situations when there is overflow of waste fluids from the underpad 210. For example, FIG. 8A shows a water proof sheet 250 uncoupled from the positioned assembly 230. The water proof sheet 250 may include a single layer or multilayer plastic sheet, water proof cloth, an absorbent sheet, or formed from any other suitable water proof material.

The water proof sheet 250 may include a plurality of first securing members (not shown) positioned on a first surface of the water proof sheet 250 facing the positioning assembly 230. In some embodiments, the first securing members may correspond to the plurality of mating securing members 224 positioned on the positioning assembly (e.g., comprise hook and loop securing members, snaps, buttons, magnets, etc.). The first securing members may be removably coupled to the plurality of mating securing members 224, or any other corresponding mating securing members positioned on the belts 232a/b of the positioning assembly 230 so as to immovably position the water proof sheet 250 on the positioning assembly 230 and, thereby on the mattress 204.

The water proof sheet 250 may also comprise a plurality of second securing members 254 positioned on a second surface 253 of the water proof sheet 250 opposite the first surface. The second securing members 254 may be positioned on the second surface 253 at locations corresponding to the locations of the securing members 222 of the underpad 210. The second securing members 254 (e.g., hook and loop securing members such as VELCRO®) are configured to be removably coupled to the securing members 222 of the underpads 210 so as to immovably position the underpad 210 on the water proof sheet 250 and, thereby the mattress 204 via the positioning assembly 230. In this manner, the water proof sheet 250 may provide added protection to the mattress 204 from soiling even in situations when the waste fluids overflow the underpad 210.

FIG. 9 is a schematic flow diagram of an example method 300 for securing an underpad (e.g., the underpad 110/210) on a mattress (e.g., the mattress 104/204). A bed sheet (e.g., a fitted bed sheet) may be positioned on the mattress. The mattress may be positioned on a box spring (e.g., the box spring 102/202) or on slats positioned on a frame (e.g., the frame 101). In some embodiments, the box spring may be positioned on the frame with the mattress disposed thereon.

The method 300 includes positioning a plurality of securing members on a lower surface of an underpad at 302. For example, the plurality of securing members 222 (e.g., hook-and-loop, magnets, snap buttons, hooks, clips or any other suitable mating securing member) may be positioned on the lower surface 211 of the underpad 110/210. The plurality of securing members 222 may be coupled to the lower surface of the underpad 110/210 via glue, staples, pins, sowing thread or any other suitable mechanism.

A first belt is positioned around the mattress at 304. A first portion of a plurality of mating securing members are positioned on the first belt. For example, the first belt 232a which includes the first portion of the plurality of mating securing members 224 is positioned around the mattress 104/204. The first portion of the plurality of mating securing members 224 may correspond to a location of a first portion of the plurality of securing members 222 positioned on the lower surface of the underpad 210.

A second belt is positioned around the mattress spaced apart from the first belt by a predetermined distance at 306. A second portion of the plurality of mating securing members positioned on the second belt. For example, the second belt 232b is positioned around the mattress 204 spaced apart from the first belt 232a by the predetermined distance. In some embodiments, a ribbon (e.g., the ribbon 234) may be coupled to each of the first belt and the second belt (e.g., the belts 232). The ribbon may have a length corresponding to predetermined distance, thereby serving as a spacer to space the first belt and the second belt by the predetermined distance.

The underpad is positioned on the mattress at 308 such that the plurality of securing members engage corresponding mating securing members so as to be removably secured thereto. In this manner, the under pad is immovably positioned on the mattress. For example, the underpad 210 having the securing members 222 positioned on the lower surface 211 thereof, is positioned on the mattress 204 such that the lower surface 211 of the underpad 210 is positioned on the mattress 204. The securing members 222 engage corresponding mating securing members 224 positioned on the belts 232 so as to be removably coupled thereto. When the underpad 210 gets dirty, the underpad 210 is removed and replaced with a new underpad 210. The underpaid 210 may have an indicator associated therewith providing a visual and/or audio indication of soiling or other condition of the underpaid 210.

In some embodiments, a water proof sheet may be interposed between the positioned first belt and second belt, and the underpad so as to provide an additional protective layer between beneath the underpad. For example, the water proof sheet 250 is interposed between the first belt 232a and the second belt 232b of the positioning assembly 230 and secured thereto as described herein. The underpad 210 may then be positioned on the water proof sheet 250 and coupled thereto as previously described, so as to secure the underpad 210 to the mattress 204 via the water proof sheet 250 and the positioning assembly 230.

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

The terms "coupled," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It should be noted that the term "example" as used herein to describe various embodiments is intended to indicate that such embodiments are possible examples, representations, and/or illustrations of possible embodiments (and such term is not intended to connote that such embodiments are necessarily extraordinary or superlative examples).

In the above description, certain terms may be used such as "up," "down," "upper," "lower," "top," "bottom," "upper," "lower," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Additionally, it should be understood that features from one embodiment disclosed herein may be combined with features of other embodiments disclosed herein as one of ordinary skill in the art would understand. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A system, comprising:
a mattress including a first mattress end extending along a longitudinal axis, a second mattress end spaced laterally away from the first mattress end and extending along the longitudinal axis, a third mattress end spaced orthogonal to the first mattress end and extending from the first mattress end to the second mattress end, and a fourth mattress end spaced longitudinally away from the third mattress end, the fourth mattress end spaced orthogonal to the first mattress end and extending from the first mattress end to the second mattress end;
an underpad positioned on the mattress such that a lower surface of the underpad is in contact with the mattress, the underpad includes an underpad frame defined by a first underpad end extending along a longitudinal axis, a second underpad end spaced laterally away from the first underpad end and extending along the longitudinal axis, a third underpad end spaced orthogonal to the first underpad end and extending from the first underpad end to the second underpad end, and a fourth underpad end spaced longitudinally away from the third underpad end, the fourth underpad end spaced orthogonal to the first underpad end and extending from the first underpad end to the second underpad end; and
a securing assembly interposed between the mattress and the underpad, the securing assembly comprising:
a plurality of underpad securing members positioned on the lower surface of the underpad along the underpad frame; and
a positioning assembly positioned over the mattress, the positioning assembly comprising a first belt, second belt, a first ribbon, a second ribbon and a plurality of mating mattress securing members,
the first belt positioned around the mattress orthogonal to a longitudinal axis of the mattress extending from the first mattress end toward the second mattress end and coupled to itself, the first belt spaced longitudinally away from the mattress third end and the mattress fourth end, the first belt including a first portion of the plurality of mating securing members positioned thereon corresponding to a first portion of the plurality of securing members,
the second belt positioned around the mattress and spaced longitudinally away from the first belt and coupled to itself, the second belt spaced longitudinally away from the mattress third end and the mattress fourth end, a second portion of the plurality of mating securing members positioned on the second belt corresponding to a second portion of the plurality of securing members,
the first ribbon is coupled to each of the first belt and the second belt and positioned orthogonal thereto, the first ribbon beginning from the first belt and terminating at the second belt such that the first ribbon has a ribbon length configured to space the first belt and the second belt apart by a predetermined distance, the predetermined distance corresponding to a spacing between the first portion of the plurality of securing members and the second portion of the plurality of securing members, and
the second ribbon is coupled to each of the first belt and the second belt and positioned orthogonal thereto, the second ribbon beginning from the first belt and terminating at the second belt such that the second ribbon has the same ribbon length as the first ribbon, the second ribbon configured to space the first belt and the second belt apart by the predetermined distance, wherein each of the plurality of underpad securing members engages a corresponding mating mattress securing member so as to be removably coupled thereto, thereby immovably positioning the underpad on the mattress.

2. The system of claim 1, wherein the plurality of underpad securing members and the plurality of mating mattress securing members comprise hook-and-loop fasteners.

3. The system of claim 1, wherein the positioning assembly further comprises:
a first length adjusting mechanism operatively coupled to the first belt, the first length adjusting mechanism configured to adjust a length of the first belt positioned around the mattress so as to correspond to a width of the mattress; and
a second length adjusting mechanism operatively coupled to the second belt, the second length adjusting mechanism configured to adjust a length of the second belt positioned around the mattress so as to correspond to the width of the mattress.

4. The system of claim 3, wherein the length adjusting mechanism comprises a slide, and a ring.

5. The system of claim 1, wherein the positioning assembly further comprises:
a first snap positioned on a first end of the first belt;
a first stud positioned on a second end of the first belt opposite the first snap,
wherein the first snap is structured to removably engage the first stud so as to removably secure the first belt around the mattress;
a second snap positioned on a first end of the second belt and
a second stud positioned on a second end of the second belt opposite the second snap,
wherein the second snap is structured to removably engage the second stud so as to removably secure the second belt around the mattress.

6. The system of claim 1, further comprising:
a water proof sheet interposed between the positioning assembly and the underpad, the water proof sheet comprising;
a plurality of first securing members positioned on a first surface of the water proof sheet at locations corresponding to mating mattress securing members of the positioning assembly and configured to be removably coupled thereto so as to secure the water proof sheet on the positioning assembly; and
a plurality of second securing members positioned on a second surface of the water proof sheet opposite the first surface, the plurality of second securing members corresponding to the plurality of underpad securing members of the underpad and configured to be removably coupled thereto so as to immovably position the underpad on the mattress.

7. The system of claim 1, wherein the plurality of underpad securing members comprises a first underpad securing member, a second underpad securing member, a third underpad securing member, and a fourth underpad securing member, the first underpad securing member is spaced at a first location where the first underpad end meets the third underpad end, wherein the second underpad securing member is spaced at a second location where the first underpad end meets the fourth underpad end, wherein the third underpad securing member is spaced at a third location where the second underpad end meets the third underpad end, and wherein the fourth underpad securing member is spaced at a fourth location where the second underpad end meets the fourth underpad end.

8. A securing assembly for securing an underpad to a mattress, the mattress comprising a first mattress end extending along a longitudinal axis, a second mattress end spaced laterally away from the first mattress end and extending along the longitudinal axis, a third mattress end spaced orthogonal to the first mattress end and extending from the first mattress end to the second mattress end, and a fourth mattress end spaced longitudinally away from the third mattress end, the fourth mattress end spaced orthogonal to the first mattress end and extending from the first mattress end to the second mattress end, the securing assembly interposed between the mattress and the underpad, the securing assembly comprising:

- a plurality of underpad securing members structured to be positioned on a lower surface of the underpad, the lower surface of the underpad defined by a first underpad end extending along a longitudinal axis, a second underpad end spaced laterally away from the first underpad end and extending along the longitudinal axis, a third underpad end spaced orthogonal to the first underpad end and extending from the first underpad end to the second underpad end, and a fourth underpad end spaced longitudinally away from the third underpad end, the fourth underpad end spaced orthogonal to the first underpad end and extending from the first underpad end to the second underpad end;
- a positioning assembly structured to be positioned around the mattress the positioning assembly comprising a first belt, second belt, a first ribbon, a second ribbon and a plurality of mating securing members positioned on the positioning assembly,
    - the first belt positioned around the mattress orthogonal to a longitudinal axis of the mattress extending from the first mattress end toward the second mattress end and coupled to itself, the first belt spaced longitudinally away from the mattress third end and the mattress fourth end, the first belt including a first portion of the plurality of mating securing members positioned thereon corresponding to a first portion of the plurality of securing members,
    - the second belt positioned around the mattress and spaced longitudinally away from the first belt and coupled to itself, the second belt spaced longitudinally away from the mattress third end and the mattress fourth end, a second portion of the plurality of mating securing members positioned on the second belt corresponding to a second portion of the plurality of securing members,
    - the first ribbon is coupled to each of the first belt and the second belt and positioned orthogonal thereto, the first ribbon beginning from the first belt and terminating at the second belt such that the first ribbon has a ribbon length configured to space the first belt and the second belt apart by a predetermined distance, the predetermined distance corresponding to a spacing between the first portion of the plurality of securing members and the second portion of the plurality of securing members, and
    - the second ribbon is coupled to each of the first belt and the second belt and positioned orthogonal thereto, the second ribbon beginning from the first belt and terminating at the second belt such that the second ribbon has the same ribbon length as the first ribbon, the second ribbon configured to space the first belt and the second belt apart by the predetermined distance, wherein each of the plurality of underpad securing members engages a corresponding mating mattress securing member so as to be removably coupled thereto, thereby immovably positioning the underpad on the mattress.

9. The securing assembly of claim 8, wherein the plurality of underpad securing members and the plurality of mating mattress securing members comprise hook-and-loop fasteners.

10. The securing assembly of claim 8, wherein the positioning assembly further comprises:

- a length adjusting mechanism operatively coupled to each of the first belt and the second belt, the length adjusting mechanism configured to adjust a length of the first belt and the second belt positioned around the mattress so as to correspond to a width of the mattress.

11. The securing assembly of claim 10, wherein the length adjusting mechanism comprises a slide, and a ring.

12. The securing assembly of claim 8, wherein the positioning assembly further comprises:

- a snap positioned on a first end of each of the first belt and the second belt; and
- a stud positioned on a second end of the each of the first belt and the second belt, the second end opposite the first end,
- wherein the snap is structured to removably engage the stud so as to removably secure the first belt and the second belt around the mattress.

13. The securing assembly of claim 8, wherein the plurality of underpad securing members comprises a first underpad securing member, a second underpad securing member, a third underpad securing member, and a fourth underpad securing member, the first underpad securing member is spaced at a first location where the first underpad end meets the third underpad end, wherein the second underpad securing member is spaced at a second location where the first underpad end meets the fourth underpad end, wherein the third underpad securing member is spaced at a third location where the second underpad end meets the third underpad end, and wherein the fourth underpad securing member is spaced at a fourth location where the second underpad end meets the fourth underpad end.

\* \* \* \* \*